United States Patent [19]

Schuster et al.

[11] 4,059,404
[45] Nov. 22, 1977

[54] SWAB AND METHOD OF TAKING CELL SMEARS FOR DIAGNOSTIC EXAMINATION

[75] Inventors: Wilhelm Schuster, Frankfurt am Main; Gert Schuluter, Liederbach, Taunus, both of Germany

[73] Assignee: Battelle-Institute e.V., Frankfurt am Main, Germany

[21] Appl. No.: 671,369

[22] Filed: Mar. 29, 1976

[30] Foreign Application Priority Data

Mar. 29, 1975 Germany .............................. 2513941

[51] Int. Cl.² ......................... C12K 1/10; A61B 10/00
[52] U.S. Cl. ................................ 23/230 B; 128/2 W; 195/139; 23/259; 23/253 TP
[58] Field of Search ................. 23/259, 230 R, 230 B, 23/253, 292; 128/2 W; 195/139

[56] References Cited
U.S. PATENT DOCUMENTS

| 3,579,303 | 5/1971 | Pickering | 23/259 X |
| 3,783,106 | 1/1974 | Henshilwood | 128/2 W |
| 3,890,204 | 6/1975 | Avery | 128/2 W |
| 3,890,954 | 6/1975 | Greenspan | 128/2 W |

Primary Examiner—R.E. Serwin
Attorney, Agent, or Firm—Bruce H. Troxell

[57] ABSTRACT

A device for taking a cell smear comprised of an applicator and a swab located on the end portion of the applicator, the swab is used to collect the cellular material when the cell smear is taken. The swab consisting of a material which is soluble in a solvent that has no detrimental effect on, or is innocuous to, the collected cellular material.

A method of taking cell smears for diagnostic examination which comprises collecting a specimen of or from the skin, mucous membrane or other body area or surface to be examined by means of a swab, which is described above. The swab is dissolved in a solvent that has no detrimental effect on, or is innocuous to, the collected cellular material in the specimen. A solution is formed containing the cellular material. The cellular material is then diagnostically examined.

7 Claims, 4 Drawing Figures

SWAB AND METHOD OF TAKING CELL SMEARS FOR DIAGNOSTIC EXAMINATION

BACKGROUND OF THIS INVENTION

1. Field of this Invention

This invention relates to a new method of taking cell smears for diagnostic examination in which a specimen of the skin, a mucous membrane or other body area to be examined is collected by means of a swab and diagnostically examined. This invention also relates to a new type of swab specially developed for use in such method.

2. Prior Art

Cell smears are taken from the skin, a mucous membrane or other body area by means of a swab and then applied to a glass slide. This type of sampling is of great importance in gynecological cytology or for smear examinations in other medical disciplines, e.g., in dermatology, in surgery (collecting cellular material from the bronchus or the esophagus) and in gastroenterology (collecting cells from the stomach and other regions of the intestinal tract).

The methods of sampling in general have been repeatedly modified in the last few years with a view to improving the diagnostic value which depends to a large extent on the sampling technique. Among the instruments used in gynecology for taking cell smears are hard implements, such as tongue blades, concave wooden spatulas and Ayre's spatulas of similar shape [*Wied*, (1974) *Soost*, (1974); and *Wheeless and Oderdonk*, (1974)]. But at the present time preference is given to cotton swabs, which have the advantage of causing less mucosal lesion during sampling. Moreover, a cotton swab can be prepared in the dimension most favorable for the site of sampling.

In gynecology smears are usually taken by collecting cells from the vaginal cavity, from the portio surface and from the cervical canal and applying them to a glass slide, which is then examined microscopically after Papanicolaou staining.

In cancer diagnostics, for example, early recognition of the disease is dependent not only on careful cell sampling adjusted to the site of cancer generation but particularly on obtaining a representative specimen of the cellular material suitable for evaluation, because frequently even very few cells of small size may determine the result of the diagnosis.

The most important demands made by cytopathologists upon the specimen to be examined may therefore be summarized as follows:

a. a qualitatively adequate supply of cells on the slide; and b. a cell pattern without mechanical cell lesions (artifacts of preparation).

If the specimens sent to the laboratory by gynecologists and, in particular, by general practitioners are evaluated with respect to these criteria, it is found that for a certain percentage of these specimens a cytological diagnosis is not possible, or only with reservations, mainly because too little cellular material is contained in the smears. As a consequence, many patients have to be given reappointments for taking a second smear. Gynecologists experienced in prescreening report that these patients often do not come again or, experiencing the "fear of cancer", are exposed to intense psychic stress.

The cellular material taken with a cotton swab and applied to a glass slide does not always meet the diagnostic requirements even if the necessary conditions are fully satisfied. The smear spread on the slide is only a part of the total specimen collected with the swab and, therefore, is not necessarily representative of possible pathological changes at the site of sampling. It was found that many cells keep adhering to the surface of the swab and especially between the cotton fibers. A good smear on a slide normally contains 15,000 to 25,000 cells; however 50 percent or more of the total specimen is left in the cotton swab and is lost for the diagnostic evaluation unless recovered by additional complicated washing processes and then converted into a suspension.

BROAD DESCRIPTION OF THIS INVENTION

An object of this invention is to provide a process of taking cellular smears and preparing such for diagnostical examination which avoids the prior art problems described above. Another object of this invention is to provide a swab which allows such process to be achieved. Another object is to provide such a process that allows collection of the total cellular material in the smears so that such total cellular material can be quantitatively and qualitatively evaluated. Another object of this invention is to provide a method of taking a cellular smear and preparing such for diagnostical examination which does not detrimentally effect the morphological and cytochemical properties of the cellular material. Other objects and advantages of this invention are set our herein or are obvious herefrom to one ordinarily skilled herein.

The objects and advantages of this invention are achieved by the process and swab of this invention.

This invention avoids the above-described disadvantages of taking cell smears by means of a cotton swab and ensures that the total material sampled can be applied to the slide for examination and evaluation of the diagnosis. An uncontrollable selection of the cellular material, e.g., the separation of small particles adhering more firmly to the swab, is prevented by this invention with the result that there is no distortion or falsification of the diagnosis. The method of this invention involves a swab that is produced from a material which is soluble in a solvent having no detrimental effect on the collected cellular material and includes dissolving such swab after sampling, followed by investigating the cellular material contained in the solution.

The swab and method of this invention ensures in a unexpectedly simple manner that all of the cells collected can be subjected to further examination, e.g., in a microscope, without the occurrence of any selection in the entire process from taking the smear to its microscopic examination.

In an preferred embodiment of this invention, the solution consisting of solvent and dissolved swab material is separated from the cellular material, e.g., by means of a centrifuge, prior to the diagnostic examination of the cellular material. In another preferred embodiment of the invention, the cellular material contained in the swab is prefixed, e.g., by the addition of ethanol, before the solvent for the swab material) is added.

DETAILED DESCRIPTION OF THIS INVENTION

Figures 1, 2, 3, 4:
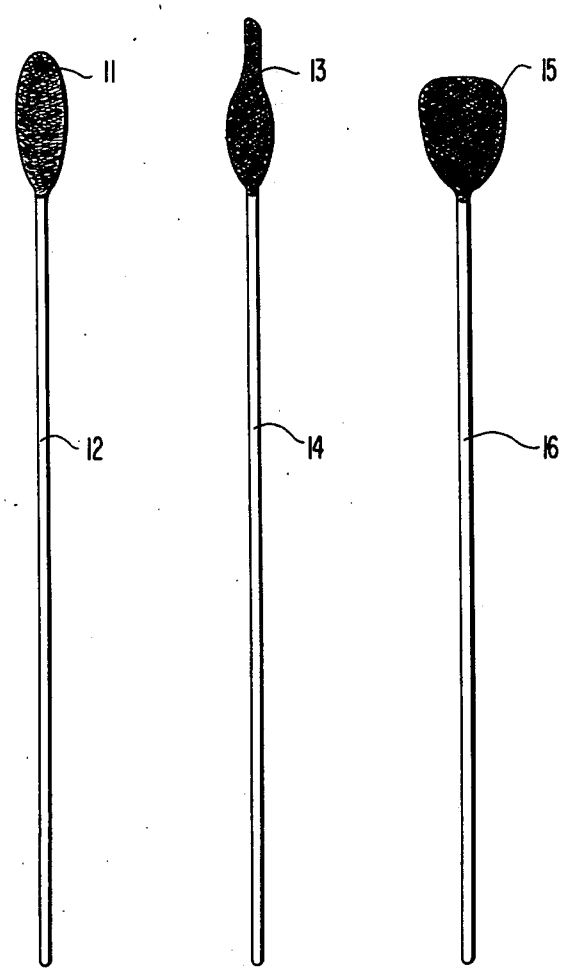
FIG. 1 is a side view of a swab, having a particular shape, of this invention on an applicator.
FIG. 2 is another swab, having a different shape, of this invention on an applicator.
FIG. 3 is a side view of still another swab, having still a different shape, of this invention on an applicator.
FIG. 4 schematically illustrates a swab of this invention on an applicator during the process of this invention.

The swab shown in FIG. 1 is designed for large-area smears and resembles in its shape the swabs commonly used for this purpose. However, according to this invention, the swab consists of a soluble material, which is preferably cellulose—2 ½-acetate. In FIG. 1 the swab is denoted by 11 and the applicator (or handle) by 12. The swab in FIG. 2 is a special shape designed for taking cellular material from the cervical canal and from the portio. In FIG. 2 the swab is denoted by 13 and the applicator by 14. The swab consists of a soluble material. In FIG. 3 the swab is made of a soluble non-woven fabric. The swab can be used in combination with an endoscope for taking specimens from the stomach or other regions of the intestinal tract, from the esophagus or the bronchus. In FIG. 3 the swab is designated by 15 and the applicator by 16. FIG. 4 shows schematically how swab 11 after collection of the cellular material is dissolved. After swab 11, attached to the applicator 12 and after treatment with a cell-fixed fluid, has been placed in conical vessel 17 filled with solvent 18, (for the swab material), for example, acetone or a mixture of acetone and water, swab 17 dissolves and total cellular material 19 obtained by the smear settles in conical vessel 17. The cellular material 18 (not shown in FIG. 4) be separated from the solvent, e.g., by means of a centrifuge. In this way, contrary to taking cell smears with conventional swabs, the total cellular material is collected and can be evaluated quantitatively and qualitatively.

A suitable swab for carrying out the method of this invention can be made of a textile fiber material, e.g., a cellulose derivative or of polyvinyl alcohol. If the swab is made of fibrous cellulose- 2 ½-acetate, it can easily be dissolved in acetone. On the other hand, the swab may also be made of a foamed material or of any other material that can be dissolved without any detrimental effect on the morphological and cytochemical properties of the specimen.

Any standard applicator can be used, although preferably the applicator is an elongated stick having a circular cross-section.

EXAMPLE

For the use of gynecological smears in the early diagnosis of cancer, swabs were prepared from textile fibers made of cellulose-2 ½-acetate. After taking smears from vagina, portio and cervical canal, each swab was placed in a vessel containing 70-percent ethanol in order to prefix the cells of the gynecological smears. After removal from the ethanol, each swab was placed in a vessel containing pure acetone- the cellulose-2 ½-acetate fibers completely dissolved within a short period of time. In order to remove the polymer dissolved in the acetone, the suspension of the cellular material was centrifuged and then washed in the centrifuge twice with acetone and once with Ringer solution. The cells collected in this way were then examined by conventional diagnostic techniques. As was shown by numerous comparative experiments using conventional instruments, e.g., ordinary cotton swabs, the method of this invention yielded a multiple of the cellular material normally recovered from a smear. The cellular material thus obtained did not exhibit any lesion or changes.

What is claimed is:

1. A method of taking cell smears for diagnostic examination comprising the steps of:
    a. collecting a cellular specimen of or from the skin, mucous membrane or other body area or surface to be examined by means of a swab located on applicator;
    b. dissolving said swab in a solvent that has no detrimental effect on the collected cellular material in the speimen whereby a solution is formed containing said cellular material; and
    c. diagnostically examining said cellular material.

2. A method as described in claim 1 wherein said cellular material is removed from said solution prior to said diagnostic examination of said cellular material.

3. A method as described in claim 2 wherein said cellular material is separated from said solution by centrifugal force.

4. A method as described in claim 1 wherein said cellular material contained in and on said swab is prefixed before said swab is dissolved in said solvent.

5. A method as described in claim 4 wherein said prefixing is achieved by treating said swab with ethanol.

6. A method as described in claim 1 wherein said swab consists of fibrous cellulos-2 ½-acetate and wherein said solvent is acetone.

7. A method as described in claim 1 comprising the further step of placing said cellular material on a glass slide before said cellular material is diagnostically examined.

* * * * *